United States Patent [19]
Mochida

[11] Patent Number: 5,957,834
[45] Date of Patent: Sep. 28, 1999

[54] ENDOSCOPE SYSTEM

[75] Inventor: Akihiko Mochida, Hino, Japan

[73] Assignee: Olympus Optical Co., Ltd., Japan

[21] Appl. No.: 09/080,831

[22] Filed: May 18, 1998

[51] Int. Cl.$^6$ .................................................. A61B 1/04
[52] U.S. Cl. ........................................ 600/180; 600/181
[58] Field of Search ................................... 600/180, 181; 348/229, 68

[56] References Cited

U.S. PATENT DOCUMENTS

| | | | |
|---|---|---|---|
| 4,791,479 | 12/1988 | Ogiu | 358/98 |
| 4,868,645 | 9/1989 | Kobayashi | 600/180 |
| 4,884,133 | 11/1989 | Kanno | 600/180 |
| 4,928,172 | 5/1990 | Uehara | 600/180 |
| 4,967,269 | 10/1990 | Sasagawa | 600/180 |
| 5,408,263 | 4/1995 | Kikuchi | 348/229 |

*Primary Examiner*—John P. Leubecker
*Assistant Examiner*—Ira Hatton
*Attorney, Agent, or Firm*—Ostrolenk, Faber, Gerb & Soffen, LLP

[57] ABSTRACT

An endoscope system includes an imaging unit for converting an image of an object into an image signal, and an automatic amount-of-light setting circuit for setting an amount of light output from a light source apparatus on the basis of the image signal provided by the imaging unit. According to a setting signal sent from the automatic amount-of-light setting circuit, the amount of light output from the light source apparatus is adjusted. Aside from the automatic amount-of-light setting circuit, a device used to set an amount of light manually is included. The automatic amount-of-light setting circuit and manual amount-of-light setting device can be switched selectively by means of a switch. Consequently, a drawback of the automatic amount-of-light setting circuit occurring when the endoscope is removed from a human body, that is, the drawback that when control is given for lowering the level of the image signal, the amount of light is increased will not take place. Control can be given for decreasing the amount of source light.

7 Claims, 6 Drawing Sheets

ENDOSCOPE SYSTEM

BACKGROUND OF THE INVENTION

1. Field of the Invention

This invention relates to an endoscope system including a light source apparatus for supplying illumination light to an endoscope in which light adjustment is controlled according to an upgraded sequence.

2. Description of the Related Art

In recent years, an endoscope having an elongated insertion unit has prevailed in the field of medicine. The insertion unit is inserted into a body cavity and thus enabling diagnosis of a lesion or the like in the body cavity without the necessity of incising it, or if necessary, enabling insertion of a treatment instrument into the body cavity for the purpose of cure.

Illumination light emanating from a light source apparatus or the like is propagated to the distal part of the insertion unit over a light guide or the like. The illumination light is irradiated to an object region such as a lesion via an illumination optical system through the distal part. An image of the object region such as a lesion is formed by an objective lens located in the distal part of the insertion unit. An optical image is transmitted to an eyepiece unit by means of an optical transmission means. An eyepiece optical system then enables the optical image to be viewed.

The optical transmission means varies depending on the usage or purpose of use. For example, a fiber bundle is used for a flexible endoscope, while a relay lens is used for a rigid endoscope.

In an electronic endoscope, which includes a solid-state imaging device, (for example, a CCD) in the distal part of an insertion unit, an optical image is formed on the image formation surface of the CCD via an objective lens. The CCD photoelectrically converts the optical image so as to provide image information in the form of an electrical signal. The image information is subjected to various kinds of image processing, and thus a desired image of an object region is displayed on a monitor or the like.

In recent years, image processing techniques have greatly improved. With the improved techniques, various kinds of image processing can be performed on the image information. For example, an endoscopic image can be enlarged, an image of a lesion or the like can be processed, or relevant images can be compared with each other. This leads to easy and accurate diagnosis. This kinds of processing of endoscopic images can be achieved even in an endoscope having a conventional optical transmission means. That is to say, when a camera head having a CCD or the like located in an eyepiece unit is freely detachably attached to the endoscope having a conventional optical transmission means, an optical image can be converted photoelectrically and processed in the form of image information.

An image produced by the foregoing electronic endoscope suffers from problems since a distance from the distal part of the insertion unit to an object is variable. If an object such as lumina or a quite irregular object must be imaged, irregular illumination occurs to being about a phenomenon that halation happens to a near object in the same picture but a far object becomes too dark to be visible.

For coping with the problem of irregular illumination, the prior art has proposed a technique of adjusting the light emanating from a light source apparatus by controlling a diaphragm drive circuit, which is included in the light source apparatus and supplies illumination light to an endoscope.

The light control is accomplished according to a light adjustment signal produced from an image signal sent from a CCD. This prior art technique alleviates the irregular illumination and is disclosed in, for example, Japanese Unexamined Patent Publication No. 62-155689.

However, when an endoscope is removed from a human body, the amount of source light emanating from a light source apparatus should preferably be decreased. When the endoscope is removed from a human body, since an object to be illuminated by the light source apparatus disappears, the level of a video signal is lowered. A light adjustment unit described in the Japanese Unexamined Patent Publication No. 62-155689 controls the diaphragm drive circuit in the light source apparatus according to the light adjustment signal produced from the image signal. Upon removal of the endoscope from the body, since the level of the video signal is lowered, the diaphragm drive circuit is controlled so that the amount of light emanating from the light source apparatus will be increased. This poses a problem that it becomes impossible to simultaneously control the source light so as to decrease the amount of source light.

OBJECTS AND SUMMARY OF THE INVENTION

An object of the present invention is to provide an endoscope system in which an image signal is not used to produce a light adjustment signal. Rather, a light source apparatus is controlled by a signal processing apparatus independent of the image signal, and an amount of light can be adjusted optimally even when an endoscope is removed from a human body.

Another object of the present invention is to provide an endoscope system in which when an endoscope is removed from a human body, a switch can be operated in order to manually adjust and control the amount of light emanating from a light source apparatus.

Furthermore, an object of the present invention is to provide an endoscope system in which the output level of a video signal produced by a solid-state imaging device is optimally controlled by controlling a charge accumulation time relevant to the solid-state imaging device. The amount of light emanating from a light source apparatus is optimally controlled by controlling the position of a diaphragm included in the light source apparatus according to a signal sent from a signal processing apparatus. Thus a problem such as a burn of an incidence end of a light guide can be solved.

Yet another object of the present invention is to provide an endoscope system in which the depth of field is improved by providing control so that the diameter of a diaphragm located in front of a solid-state imaging device will be minimal. The amount of light emanating from a light source apparatus is controlled properly. The present invention further solves a problem underlying a prior art that when the diaphragm in a camera head is controlled in order to improve the depth of field, the amount of light emanating from the light source apparatus cannot be controlled at an imaging apparatus. In a mode of the present invention for improving the depth of field by controlling the diaphragm in the camera head, if an endoscope and object are very close to each other, the amount of light emanating from the light source apparatus is decreased such that only the minimizing amount of light is emitted as necessary for narrowing down the diaphragm so as to improve the depth of field. When the endoscope and object are distanced far from each other, the light source apparatus is controlled so that a large amount of light can be emitted from the light source apparatus but the diaphragm in the camera head will not be opened.

According to the present invention, there is provided an endoscope system that includes: an endoscope having an imaging means which is inserted into a body cavity for imaging an object in the body cavity; a light source apparatus for supplying illumination light to the endoscope so as to irradiate the illumination light to the object in the body cavity via the endoscope, including a light source, a diaphragm for controlling the amount of illumination light output from the light source, a diaphragm position detecting means for detecting the position of the diaphragm, and a diaphragm control means for controlling the diaphragm according to an external light adjustment signal; an automatic amount-of-light setting means for processing an image signal sent from the imaging means in the endoscope and for setting the amount of light output from the light source apparatus on the basis of the image signal; a manual amount-of-light setting means for use in manually setting the amount of light output from the light source apparatus; a switch for selectively switching the automatic amount-of-light setting means and manual amount-of-light setting means; and a light adjustment signal producing means for inputting a setting signal sent from the automatic amount-of-light setting means or manual amount -of-light setting means selected by the switch and a position detection signal output from the diaphragm position detecting means in the light source apparatus so as to produce a light adjustment signal. The light adjustment signal produced by the light adjustment signal producing means is output as an external light adjustment signal to the diaphragm control means in the light source apparatus.

DESCRIPTION OF THE PREFERRED EMBODIMENTS

Figure 1:
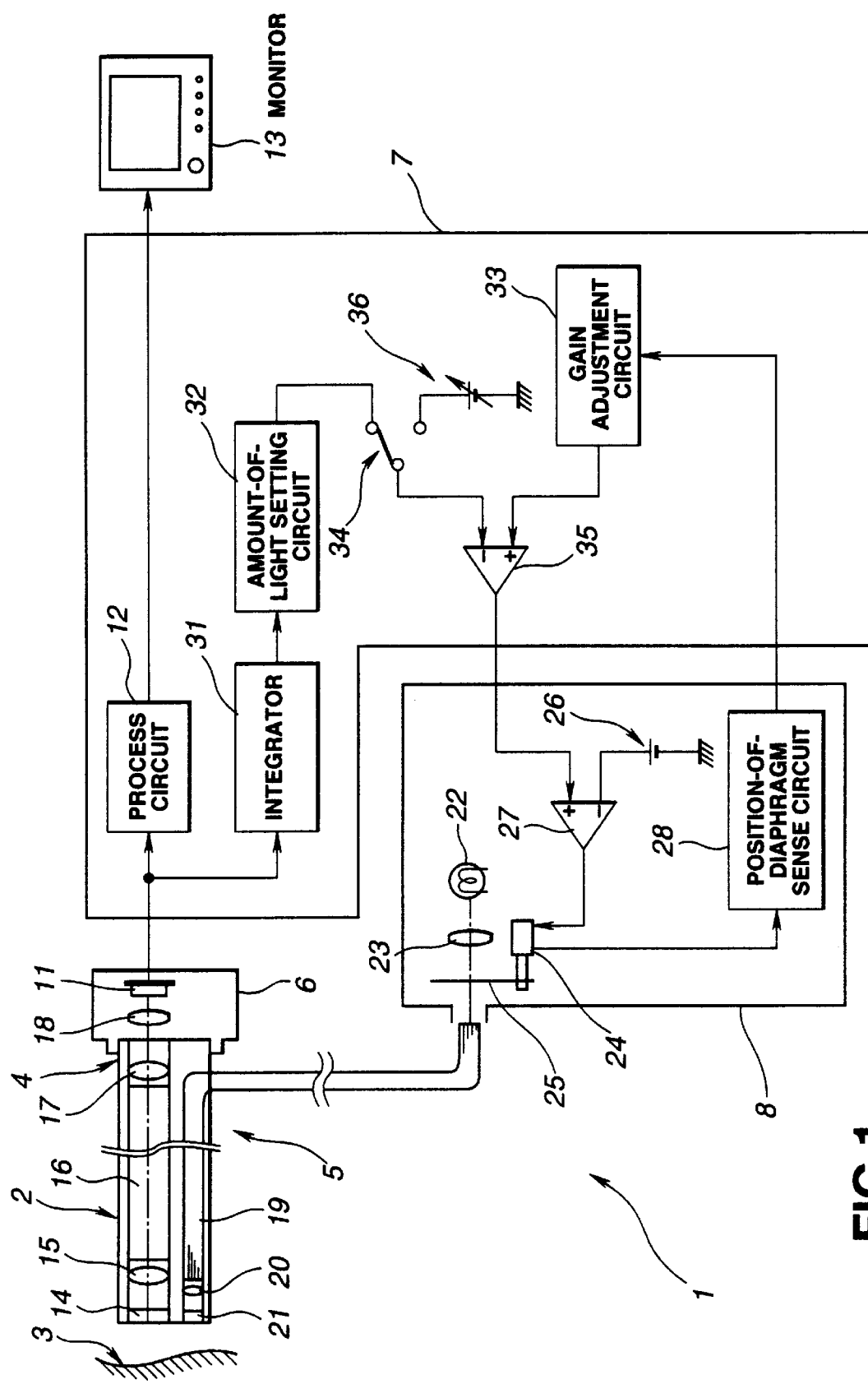
FIG. 1 is a diagram showing the configuration of an endoscope system of the first embodiment.

Referring to the drawings, embodiments of the present invention will be described below.

Figure 2:
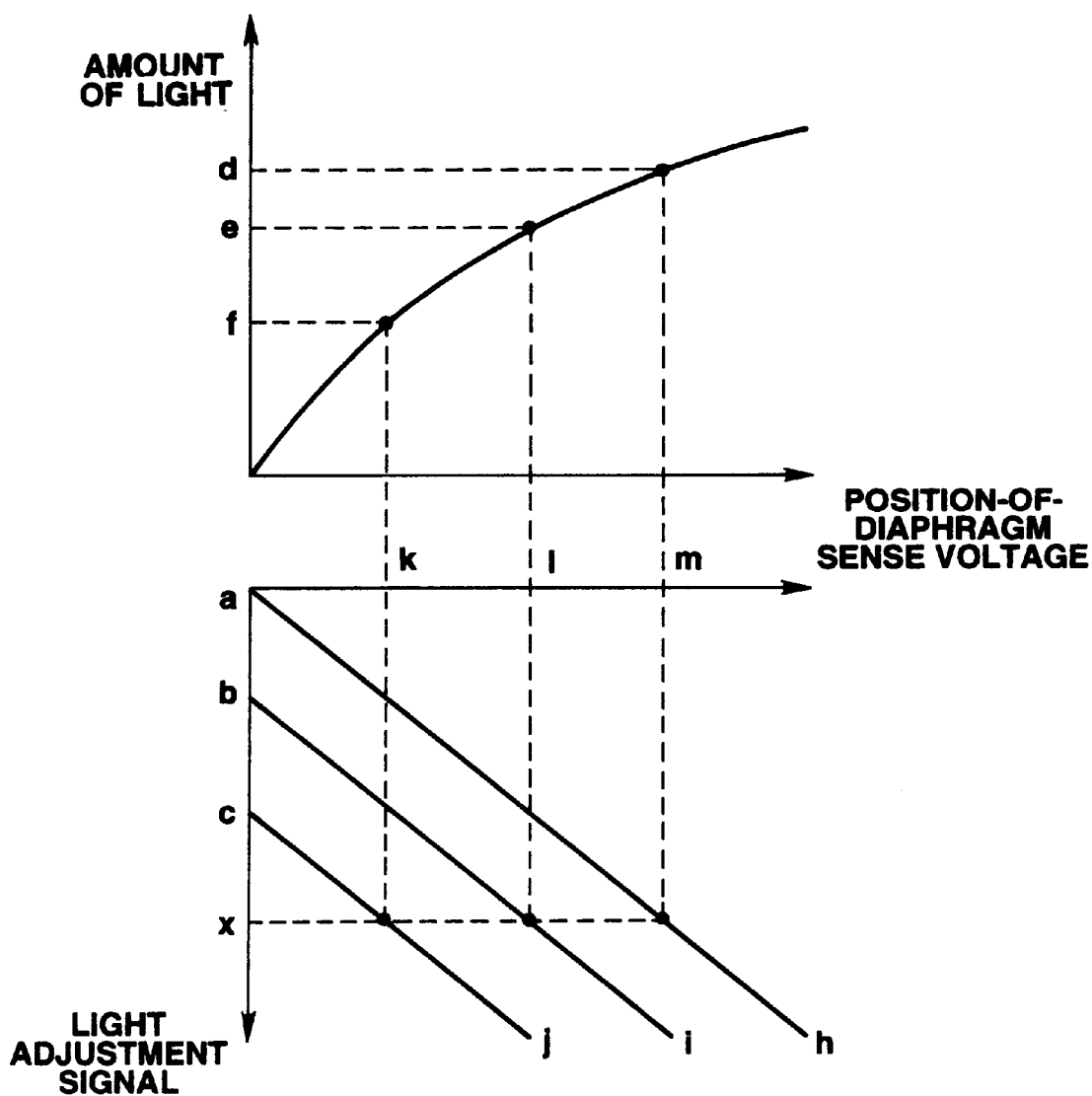
FIG. 2 is illustrating the operation of a signal processing apparatus in the endoscope system shown in FIG. 1.

FIGS. 1 and 2 relate to the first embodiment of the present invention. FIG. 1 is a diagram showing the configuration of an endoscope system, and FIG. 2 is an explanatory diagram for explaining the operation of a signal processing apparatus in FIG. 1.

As shown in FIG. 1, an endoscope system 1 of this embodiment includes a rigid endoscope 5 having an insertion unit 2 that is inserted into a body cavity and produces an optical image of an object 3, such as a lesion. The optical image is transmitted to an eyepiece unit 4. A camera head 6 is freely detachably attached to the eyepiece unit 4 of the rigid endoscope 5, for capturing the optical image. A signal processing apparatus 7 processes an image signal produced by the camera head 6. A light source apparatus 8 supplies illumination light to the rigid endoscope 5.

The optical image of the object 3 transmitted to the eyepiece unit 4 of the rigid endoscope 5 is converted into an image signal by a solid-state imaging device in the camera head 6, for example, a CCD 11. The image signal is then sent to the signal processing apparatus 7. In the signal processing apparatus 7, the image signal is processed by a process circuit 12, and transmitted as a video signal to a monitor 13. Consequently, the object 3 can be viewed by means of the monitor 13.

The rigid endoscope 5 takes the optical image of the object 3 through an observation window 14 located in the distal part of the insertion unit 2. The optical image is routed to the incidence surface of a relay lens 16 by way of an objective lens 15, and then transmitted to the eyepiece unit 4 by the relay lens 16. The eyepiece unit 4 has an eyepiece 17. The optical image is formed on the image formation surface of the CCD 11 by an objective optical system 18 in the camera head 6 attached to the eyepiece unit 4 through the eyepiece 17.

The rigid endoscope 5 includes a light guide 19 disposed in the insertion unit 2 and extending from a proximal side so as to be freely detachably attached to the light source apparatus 8. The light guide 19 propagates illumination light supplied from the light source apparatus 8 to the distal part of the insertion unit 2, and irradiates the illumination light to the object 3 via an illumination lens 20 and illumination window 21 through the emission surface thereof.

The light source apparatus 8 includes a lamp 22 for emitting illumination light, a condenser 23 for converging the illumination light emanating from the lamp 22 on the incidence surface of the light guide 19, a diaphragm 25 for adjusting the amount of illumination light passing through the condenser 23 when driven by a motor 24, a comparator 27 for comparing a light adjustment signal, which will be described later, sent from the signal processing apparatus 7 with a reference value 26 so as to control the diaphragm, and a position-of-diaphragm sense circuit 28 for sensing the position of the diaphragm 25 controlled by the comparator 27 and outputting it to the signal processing apparatus 7.

The signal processing apparatus 7 includes, in addition to the aforesaid process circuit 12, an integrator 31 for inputting an image signal from the CCD 11 in the camera head 6 and integrating the components of the image signal produced during one field, an amount-of-light setting circuit 32 for setting the amount of light emanating from the light source apparatus 8 to a set value on the basis of the result of integration performed by the integrator 31, a gain adjustment circuit 33 for adjusting a gain on the basis of a position-of-diaphragm sense signal sent from the position-of-diaphragm sense circuit 28 in the light source apparatus 8, and an adder-subtractor 35 for adding or subtracting an output of the gain adjustment circuit 33 to or from an output provided by the amount-of-light setting circuit 32 via a switch 34 so as to produce a light adjustment signal, and outputting the light adjustment signal to the comparator 27 in the light source apparatus 8.

The switch 34 is mounted, for example, on an operation panel, (not shown) for use in switching an automatic control mode in which light adjustment is controlled automatically according to the light adjustment signal produced from the image signal and a manual control mode in which light adjustment is manually controlled. When the manual control mode is selected by the switch 34, a manual amount-of-light setting device 36 to be set using a setting knob located, for example, on the operation panel that is not shown provides an output to the adder-substractor 35 in place of the amount-oflight setting circuit 32.

Next, the operation of this embodiment having the foregoing components will be described.

At the upper half of FIG. 2 is a graph representing the relationship between a position-of-diaphragm sense signal (voltage signal) provided by the provided by the position-of-diaphragm sense circuit 28 and an amount of light emitted from the light source apparatus 8. At the lower half of FIG. 2 is a graph representing the relationship between the position-of-diaphragm sense signal (voltage signal) provided by the position-of-diaphragm sense circuit 28 and a light adjustment signal produced by the signal processing apparatus 7. The value "x" in the graph of FIG. 2 indicates the reference value 26. The light adjustment signal sent from the adder-substractor 35 is controlled by the light source apparatus 8 so that it will assume the "x" value at last.

Referring to FIGS. 1 and 2, a procedure of controlling light adjustment performed by the light source apparatus 7 using a position-of-diaphragm sense signal (voltage signal) produced by the position-of-diaphragm sense circuit 28 will be explained in detail.

An operation of the signal processing apparatus 7 performed when the switch 34 is set in the manual control mode (lower position) will first be described.

A gain of the position-of-diaphragm sense signal (voltage signal) provided by the position-of-diaphragm sense circuit 28 is adjusted by the gain adjustment circuit 33 so that the level of the position-of-diaphragm sense signal will match the one of the light adjustment signal requested by the light source apparatus 8. The values "a", "b" and "c" in FIG. 2 indicate values deduced from a set value which is set by setting device 36. When the set value is varied by manually adjusting the setting knob (manually light adjustment setting device 36) located on the operation panel (not shown), the diaphragm 25 in the light source apparatus 8 is controlled by the signal processing apparatus 7.

Referring to FIG. 2, assuming that a manually set value is the "a" value, a straight line "h" extending from "a" in FIG. 2 is referenced. When the light adjustment signal represented by the straight line "h" assumes the "x" value, the position-of-diaphragm sense signal (voltage signal) assumes an "m" value. In relation to "m," an amount of light "d" is emitted from the light source apparatus 7.

Next, assuming that the set value is "b," a straight line "i" in FIG. 2 is referenced. When the light adjustment signal represented by the straight line "i" assumes the "x" value, the position-of-diaphragm sense signal (voltage signal) assumes a value of "1.". At this time, an amount of light "e" is emitted from the light source apparatus 8.

Likewise, assuming that the set value is "c," a straight line "j" is referenced. When the light adjustment signal represented by the straight line "j" assume the "x," value, the position-of-diaphragm sense signal (voltage signal) assumes the value of "k". When the position-of-diaphragm sense signal (voltage signal) assumes "k", an amount of light "f" is emitted by the light source apparatus 8.

Providing the control described above, the amount of light emanating from the light source apparatus 8, that is, the diaphragm 25, can be controlled by the signal processing apparatus 7.

Next, a description will be made of the automatic control mode in which the switch 34 is set to the upper side in FIG. 1. In this case, an image signal captured by the CCD 11 is integrated by the integrator 31 in units of a field or frame. Thus, an average value of the captured signal is calculated.

The result of integration is sent to the amount-of-light setting circuit 32. The amount-of-light setting circuit 32 produces a voltage indicated with a point in FIG. 2, sends it to the adder-substractor 35, and thus gives control on the basis of the image signal so that the amount of light emanating from the light source apparatus 8 will be set to a proper value.

In this embodiment, light adjustment performed by the light source apparatus 8 may be controlled on the basis of the image signal captured by the CCD 11 or may be manually controlled irrespective of the image signal. Consequently, even when the rigid endoscope 5 is removed from a body cavity, or when a video signal represents a dark image but the diaphragm in the light source apparatus 8 must be narrowed down, the diaphragm 25 can be controlled by the signal processing apparatus 7. This results in improved safety.

This embodiment has been described with respect to a configuration for producing an object image by means of a rigid endoscope and camera head. Needless to say, even when the embodiment is adapted to a configuration in which an electronic endoscope or soft endoscope that has a solid-state imaging means such as a CCD is included in the distal part of an insertion unit is combined with the camera head, the same operation and advantage can be exerted.

Figure 3:
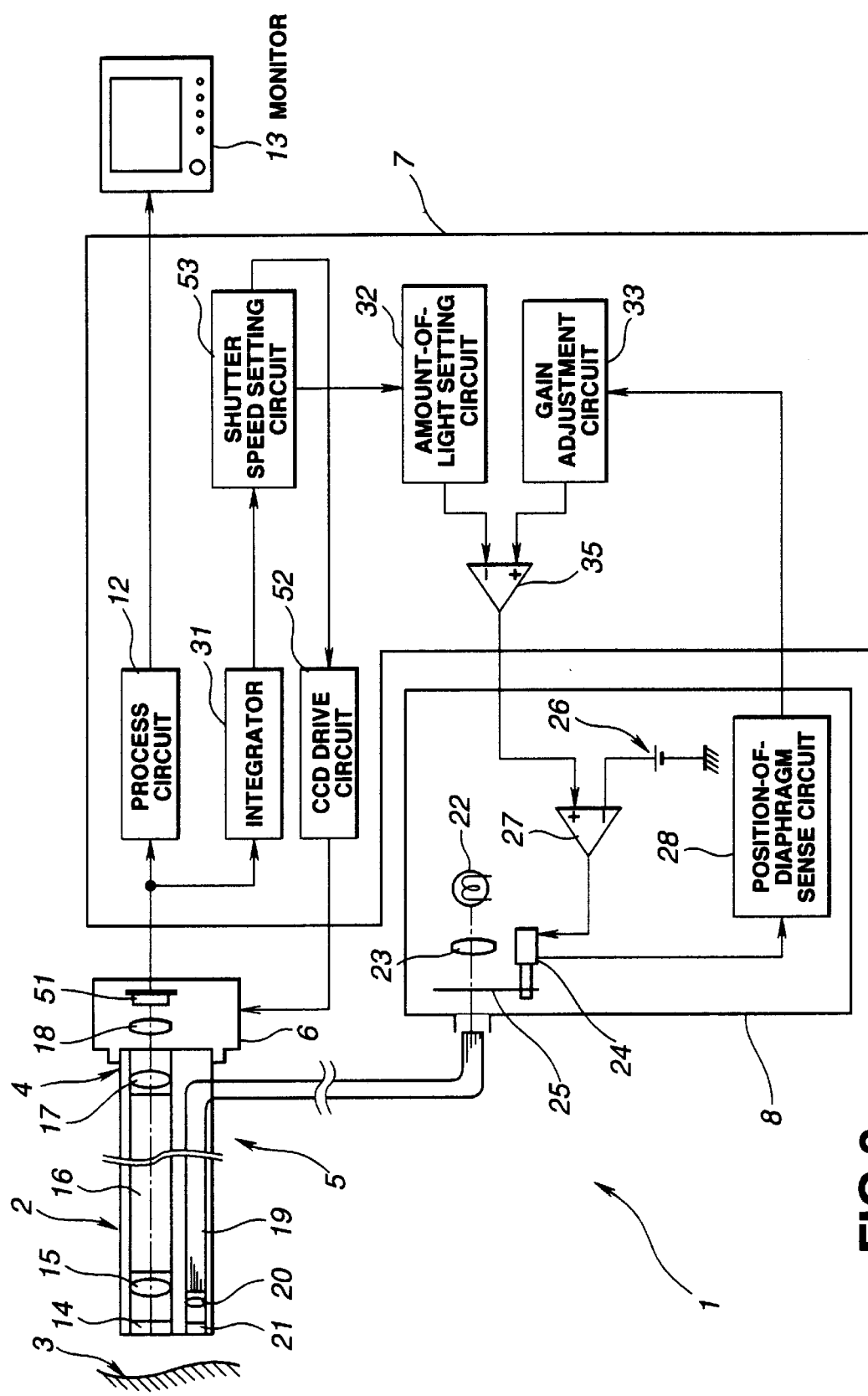
FIG. 3 is a diagram showing the configuration of an endoscope system of the second embodiment.
Figure 4:
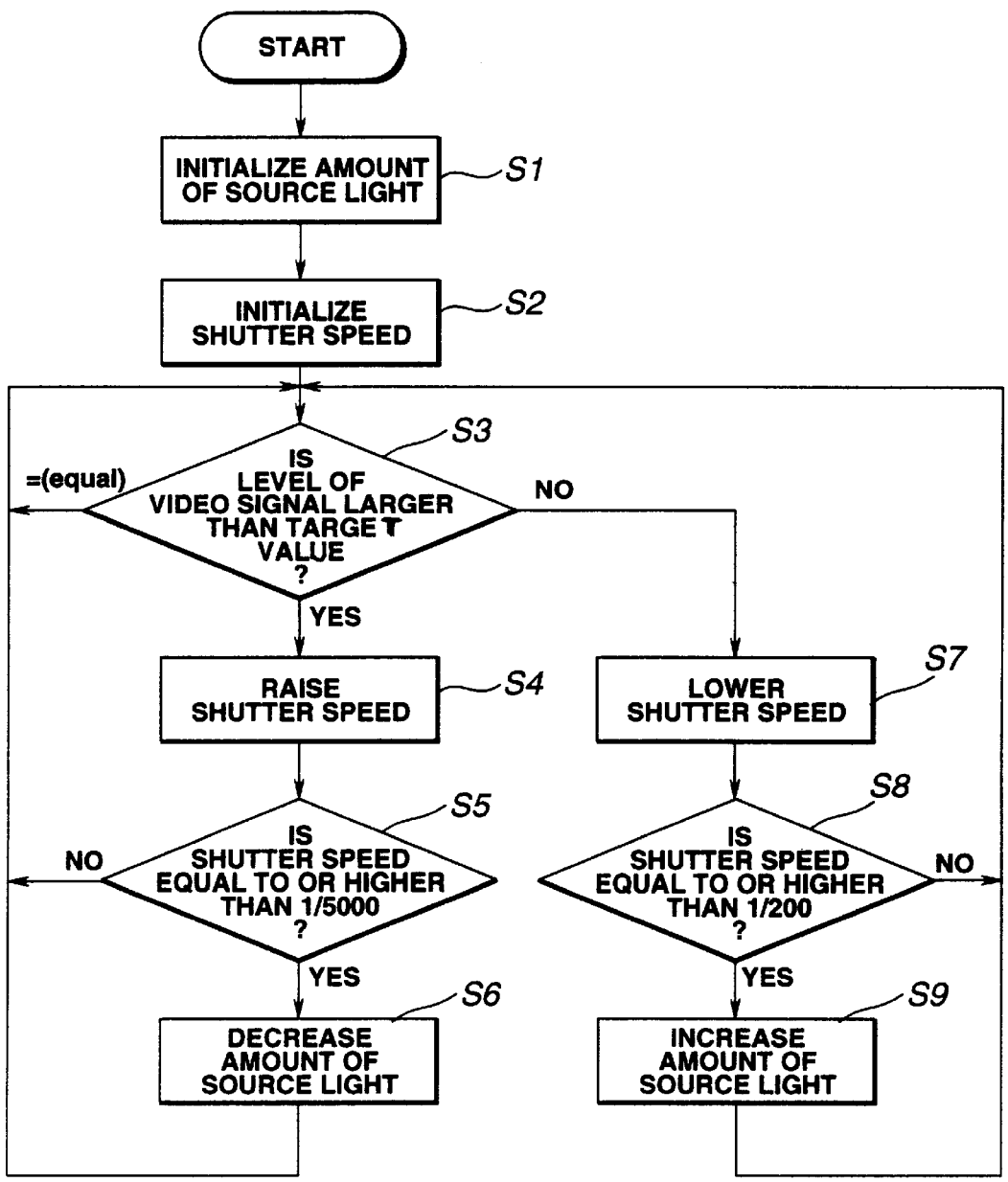
FIG. 4 is a flowchart describing the operation of the endoscope system shown in FIG. 3.

FIGS. 3 and 4 relate to the second embodiment of the present invention. FIG. 3 is a diagram showing the configuration of an endoscope system, and FIG. 4 is a flowchart describing the operation of the endoscope system shown in FIG. 3.

The second embodiment is almost identical to the first embodiment and only the differences will be described. The same reference numerals will be assigned to components identical to those of the first embodiment, and the description of the components will be omitted. Although not shown with respect to this embodiment, the switch 34 and the manual amount-of-light setting device 36 connected to one terminal of the switch 34 may be placed between the amount-of-light setting circuit 32 and the adder-substractor 35 in the signal processing apparatus 7.

As shown in FIG. 3, a CCD 51 in the camera head 6 of this embodiment is a solid-state imaging device capable of varying a charge accumulation time. The charge accumulation time can be controlled by a CCD drive circuit 52 included in the signal processing apparatus 7. Moreover, the signal processing apparatus 7 is provided with a shutter speed setting circuit 53. An integrated value of an image signal calculated by the integrator 31 is sent to the shutter speed setting circuit 53. The shutter speed setting circuit 53 determines the shutter speed of the CCD 51, that is, the charge accumulation time.

Information related to the charge accumulation time determined by the shutter speed setting circuit 53 is sent to the CCD drive circuit 52, and is sent to the amount-of-light setting circuit 32. This change accumulation time is used to produce a light adjustment signal needed for controlling the amount of light emanating from the light source apparatus 8, that is, the diaphragm 25.

The other components are identical to those of the first embodiment.

Next, the operation of this embodiment will be described in conjunction with the flowchart of FIG. 4.

As shown in FIG. 4, first the amount of light emitted from the light source is initialized to any value at step S1, and the shutter speed is initialized to any value at step S2.

At step S3, the level of an image signal sent from the CCD 51, which is calculated by the integrator 31, is compared with a target value in the shutter speed setting circuit 53.

If the result of comparison reveals that they agree with each other, it means that the current level of the image signal is equal to the target value and the state of the shutter speed is maintained.

If the level of the image signal is higher than the target value, control is provided for raising the shutter speed at step S4. Control is then passed to step S5. According to this procedure, since the charge accumulation time is shortened by raising the shutter speed, the level of the image signal is lowered.

As step S5, it is judged whether or not the shutter speed is higher or lower than, for example, $1/5000$. The value of $1/5000$ is given merely as a example. Any value will do. If the shutter speed is lower than $1/5000$, that is, if the judgment of step S5 is made in the negative, control is returned to step S3. Control is then provided for maintaining the current state as described above. If the shutter speed is equal to or higher than $1/5000$, information is sent to the amount-of-light setting circuit 32 so that the amount of source light will be decreased (see step S6). The reduction of the amount of source light may be achieved stepwise or continuously.

After the amount of source light is decreased, control is returned to step S3, at which the level of an image signal is continually compared with the target value.

The following description will be made with respect to the situation when the level of an image signal is found to be smaller than the target value at step S3.

If the level of an image signal is smaller than the target value, it means that the brightness of an image is smaller than the target value. At step S7, therefore, the CCD drive circuit 52 is controlled in order to lower the shutter speed, that is, extending the charge accumulation time.

Next, at step S8 it is determined whether or not the shutter speed is lower than, for example, $1/200$. If the shutter speed is equal to or higher than the $1/200$, the current state is maintained. Control is returned to step S3 at which the level of an image signal is compared with the target value. If the shutter speed is lower than $1/200$, control is passed to step S9 in which the amount-of-light setting circuit 32 is controlled for increasing the amount of source light.

The remainder of the operation of the second embodiment is identical to that of the first embodiment.

As mentioned above, in the second embodiment, the amount of light emanating from the light source is controlled so that the shutter speed with fall within a certain range, for example, a range from $1/200$ to $1/5000$. Thus, even when the object 3 and rigid endoscope 5 approach each other and the amount of light becomes excessive, control is provided for narrowing down the diaphragm 25 in the light source apparatus 8. A minimum necessary amount of emitted light required for adjusting light can be provided. Moreover, if the object 3 and rigid endoscope 5 are separated from each other, control is provided for increasing the amount of light emanating from the light source apparatus 8. The present invention solves the problem of a dark image that occurs because an object is located at a far point.

According to this embodiment, even when light adjustment is carried out by controlling the charge accumulation time, there is provided an advantage that a problem of a burn of a light guide deriving from an excessive amount of light or a problem that an amount of light is insufficient because an object is located at a far point will not occur.

Figure 5:
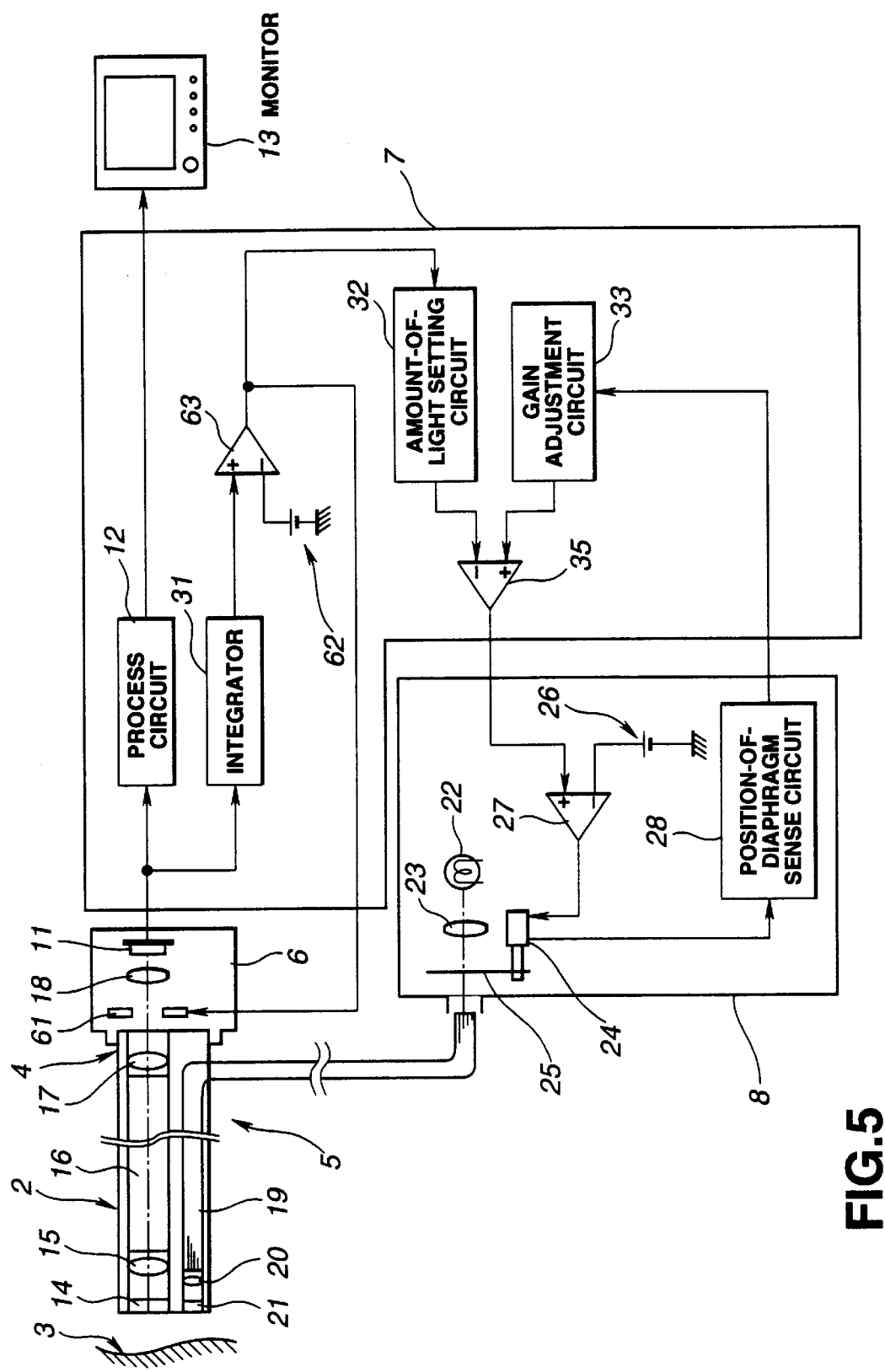
FIG. 5 is a diagram showing the configuration of an endoscope system of the third embodiment.
Figure 6:
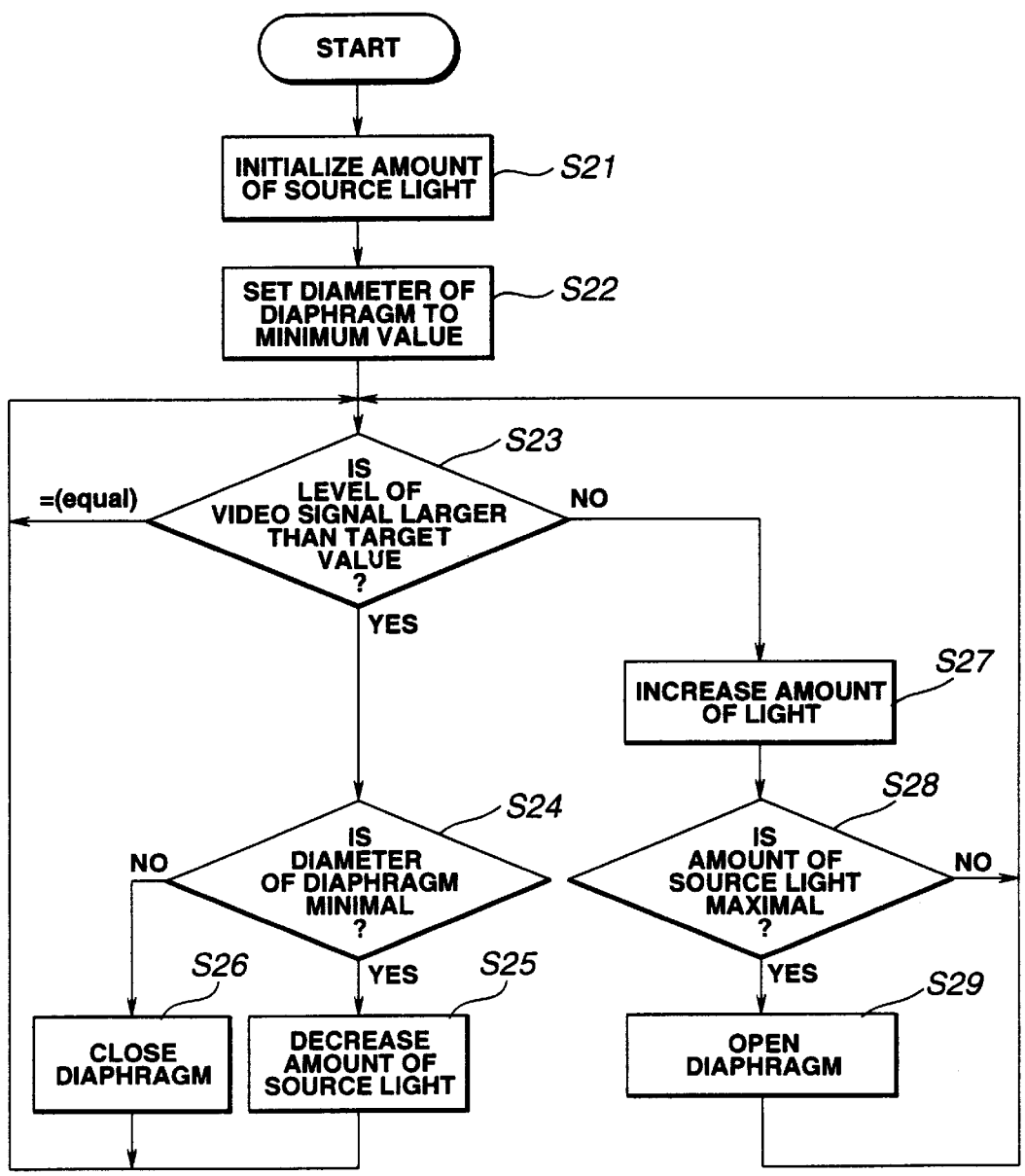
FIG. 6 is a flowchart describing the operation of the endoscope system shown in FIG. 5.

FIGS. 5 and 6 relate to the third embodiment of the present invention. FIG. 5 is a diagram showing the configuration of an endoscope system, and FIG. 6 is a flowchart describing the operation of the endoscope system shown in FIG. 5.

The third embodiment is nearly identical to the first embodiment and only the differences will be described. The same reference numerals will be assigned to components identical to those of the first embodiment, and the description of the components will be omitted. In this third embodiment, like the first and second embodiments, the switch 34 and manual amount-of-light setting device 36 (not shown) may be installed on a stage preceding the adder-substractor 35.

In this embodiment, as shown in FIG. 5, a diaphragm unit 61 is located in front of the CCD 11 in the camera head 6. The diaphragm unit 61 is used to control the light reflected from an object, whereby light adjustment is controlled. The diaphragm unit 61 is narrowed down in order to improve the depth of field of the camera head. Thus, this embodiment provides an endoscope system in which focus is unnecessary over a range from a far point to a near point.

The signal processing apparatus 7 includes a comparator 63 for comparing an average value of an image signal with a reference value 62. The average value of the image signal is calculated by integrating an image signal taken by the CCD 11 in units of one field or frame by means of the integrator 31. The reference value 62 is a target value of the image signal. The signal processing apparatus 7 thus produces a diaphragm control signal used to control the diaphragm unit 61.

The diaphragm control signal sent from the comparator 63 is also input to the amount-of-light setting circuit 32, whereby the amount of source light is controlled.

The other components are identical to those of the first embodiment.

Next, the operation of this third embodiment will be described in conjunction with the flowchart of FIG. 6.

As described in FIG. 6, in the first step, the amount of source light is initialized to any value at step S21. Next, at step S22, the diameter of the diaphragm unit 61 in the camera head 2 is set to a minimum value so that the depth of field of the camera head 2 will improve to the greatest extent.

As step S23, the comparator 63 compares the level of an image signal with the reference value 62. If the level of the image signal with the reference value agree with each other, the current state of the diaphragm unit 61 is maintained.

If the level of the image signal is larger than the reference value 62, that is, the brightness of the an image is larger than the target value, it is determined at step S24 whether or not the diameter of the diaphragm of the diaphragm unit 61 in the camera head 6 is minimal. If the diameter of the diaphragm of the diaphragm unit 61 is already minimal, control is passed to step S25. In step S25, the diaphragm 25 in the light source apparatus 8 is controlled for decreasing the amount of source light. Control is then returned to step S23.

If the diameter of the diaphragm in unit 61 is not minimal, control is passed to step S26. In step S26, the diaphragm of the diaphragm unit 61 is closed for controlling the amount of light. Control is then returned to step S23.

The following describes an operation to be carried out when it is determined at step S23 that the level of an image signal is smaller than the reference value 62 (i.e. an image is dark).

In this case, at step S27, the amount-of-light setting circuit 32 is controlled for increasing the amount of source light. At step S28, it is determined whether or not the amount of light emanating from the light source apparatus 8 is maximal. If the amount of light is not maximal, control is returned to step S23.

When the amount of light emanating from the light source apparatus 8 is maximal, control is given at step S29 so that the diaphragm unit 61 in the camera head 6 will be opened.

The remaining operation of this third embodiment is identical to that of the first embodiment.

According to the present invention, it is apparent that a wide range of different embodiments can be constructed on the basis of the invention without a departure from the spirit and scope of the invention. This invention is limited to the appended claims but not restricted to any specified embodiments.

What is claimed is:

1. An endoscope system comprising:

an endoscope including an imaging means to be inserted into a body cavity for imaging an object in said body cavity;

a light source apparatus coupled to said endoscope, said light source apparatus supplying illumination light to said endoscope so as to irradiate said illumination light to said object in said body cavity by way of said endoscope, said light source apparatus including a light source, a diaphragm for controlling an amount of said illumination light output from said light source, a position-of-diaphragm detecting means for detecting the position of said diaphragm, and a diaphragm control means for controlling said diaphragm according to a light adjustment signal; and a signal processing apparatus coupled to said endoscope and said light source apparatus, said signal processing apparatus processing an image signal received from said imaging means in said endoscope, said signal processing apparatus including an imaging device driving means for varying and controlling a charge accumulation time relevant to said imaging means, an automatic amount-of-light setting means for setting the amount of light output from said light source apparatus on the basis of said image signal, a manual amount-of-light setting means for manually setting the amount of light output from said light source apparatus, a switch for selectively switching said automatic amount-of-light setting means and said manual amount-of-light setting means, and a light adjustment signal producing means for inputting a setting signal sent from said automatic amount-of-light setting means or said manual amount-of-light setting means selected by said switch and for inputting a position detection signal output from said position-of-diaphragm detecting means in said light source apparatus so as to produce a light adjustment signal, said light adjustment signal produced by said light adjustment signal producing means being output to said diaphragm control means in said light source apparatus.

2. An endoscope system according to claim 1, wherein said signal processing apparatus produces said light adjustment signal whose level is determined so that said charge accumulation time will fall within any range.

3. An endoscope system according to claim 1, wherein said endoscope has a diaphragm means located in front of said imaging means, and said signal processing apparatus includes a control means for controlling said diaphragm means according to a level of an output of said imaging means.

4. An endoscope system according to claim 3, wherein said light adjustment signal producing means produces said light adjustment signal whose level is determined so that said diaphragm means will have a minimum diameter.

5. An endoscope system comprising:

an endoscope having a portion inserted into a body cavity;

an imaging device disposed in said endoscope and generating an image signal representing an object in said body cavity, said imaging device having a charge accumulation time;

an imaging device controller coupled to said imaging device, said imaging device controller varying said charge accumulation times;

a light source coupled to said endoscope, said light source supplying illumination light to said endoscope so as to irradiate said illumination light to said object in said body cavity;

a diaphragm disposed between said light source and said endoscope, said diaphragm controlling an amount of illumination light output from said light source;

a diaphragm position detector coupled to said diaphragm, said diaphragm generating a position detection signal in response to a position of said diaphragm;

a diaphragm controller coupled to said diaphragm and controlling said diaphragm according to a light adjustment signal;

an automatic amount-of-light setting circuit coupled to said imaging device, said automatic amount-of-light setting circuit generating a first output light level in response to said image signal generated by said imaging device, said first output light level representing a light level which has been determined should be output by said diaphragm;

a manual amount-of-light setting circuit for manually determining a second output light level, said second output light level representing said light level which has been determined should be output by said diaphragm;

a switch coupled to said automatic amount-of-light setting circuit and coupled to said manual amount-of-light setting circuit, said switch selectively outputting one of said first and said second output light levels; and a light adjustment circuit coupled to said switch, said diaphragm controller and said diaphragm position detector, said light adjustment circuit generating said light adjustment signal in response to said position detection signal generated by said diaphragm position detector and in response to the output light level output by said switch, said light adjustment signal being output to said diaphragm controller to control said diaphragm.

6. An endoscope system comprising:

an endoscope having a portion inserted into a body cavity;

an imaging device disposed in said endoscope and generating an image signal representing an object in said body cavity;

an endoscope diaphragm located in front of said imaging device;

an endoscope diaphragm controller coupled to said endoscope diaphragm and coupled to said imaging device, said endoscope diaphragm controller controlling said endoscope diaphragm means in response to a level of said image signal generated by said imaging device;

a light source coupled to said endoscope, said light source supplying illumination light to said endoscope so as to irradiate said illumination light to said object in said body cavity;

a diaphragm disposed between said light source and said endoscope, said diaphragm controlling an amount of illumination light output from said light source;

a diaphragm position detector coupled to said diaphragm, said diaphragm generating a position detection signal in response to a position of said diaphragm;

a diaphragm controller coupled to said diaphragm and controlling said diaphragm according to a light adjustment signal;

an automatic amount-of-light setting circuit coupled to said imaging device, said automatic amount-of-light setting circuit generating a first output light level in response to said image signal generated by said imaging device, said first output light level representing a light level which has been determined should be output by said diaphragm;

a manual amount-of-light setting circuit for manually determining a second output light level, said second output light level representing said light level which has been determined should be output by said diaphragm;

a switch coupled to said automatic amount-of-light setting circuit and coupled to said manual amount-of-light setting circuit, said switch selectively outputting one of said first and said second output light levels; and a light adjustment circuit coupled to said switch, said diaphragm controller and said diaphragm position detector, said light adjustment circuit generating said light adjustment signal in response to said position detection signal generated by said diaphragm position detector and in response to the output light level output by said switch, said light adjustment signal being output to said diaphragm controller to control said diaphragm.

7. An endoscope system according to claim 6, wherein said light adjustment circuit generates said light adjustment signal such that a diameter of said endoscope diaphragm is a minimum.

* * * * *